United States Patent [19]
Dassa et al.

[11] Patent Number: 5,205,830
[45] Date of Patent: Apr. 27, 1993

[54] CATHETER ASSEMBLY

[75] Inventors: Alyssa J. Dassa, Flying Hills; Philip B. Fleck, Douglassville, both of Pa.

[73] Assignee: Arrow International Investment Corporation, Wilmington, Del.

[21] Appl. No.: 791,022

[22] Filed: Nov. 12, 1991

[51] Int. Cl.⁵ ............................................. A61M 5/178
[52] U.S. Cl. ...................................... 604/164; 604/280
[58] Field of Search .............. 604/164, 166, 170, 280, 604/281

[56] References Cited

U.S. PATENT DOCUMENTS

| | | | |
|---|---|---|---|
| 2,828,744 | 4/1958 | Hirsch et al. | 604/165 |
| 3,459,189 | 8/1969 | Alley et al. | 604/170 X |
| 3,698,396 | 10/1972 | Katerndahl et al. | 604/164 |
| 4,636,199 | 1/1987 | Victor | 604/164 |
| 4,664,660 | 5/1987 | Goldberg et al. | 604/321 |
| 4,787,884 | 11/1988 | Goldberg | 604/170 X |
| 4,927,418 | 5/1990 | Dake et al. | 604/280 X |
| 4,986,814 | 1/1991 | Burney et al. | 604/166 X |

Primary Examiner—John J. Wilson
Assistant Examiner—Jeffrey A. Smith
Attorney, Agent, or Firm—Synnestvedt & Lechner

[57] ABSTRACT

Large diameter catheters for drainage of body cavities and infusion are disclosed. A removable assembly comprising a stiffening cannula, hollow dilator and wire guide facilitate insertion, reduce trauma and reduce the risk to delicate tissue. The distal tip of the stiffening cannula interfaces with a shoulder within the catheter adjacent to the tip, and insertion is accomplished by application of axial pressure on the cannula which is transmitted to the catheter via the shoulder. The tapered tip of the dilator conforms to and reinforces the pliant tip of the catheter during insertion. The catheter includes a branch line for infusion and sampling.

12 Claims, 2 Drawing Sheets

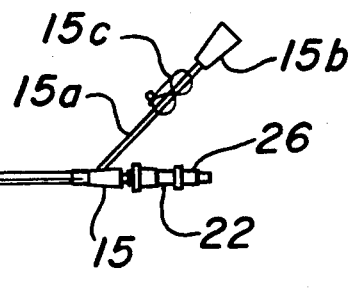
FIG. 1
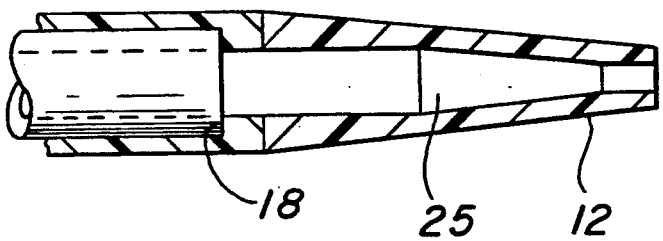
FIG. 5
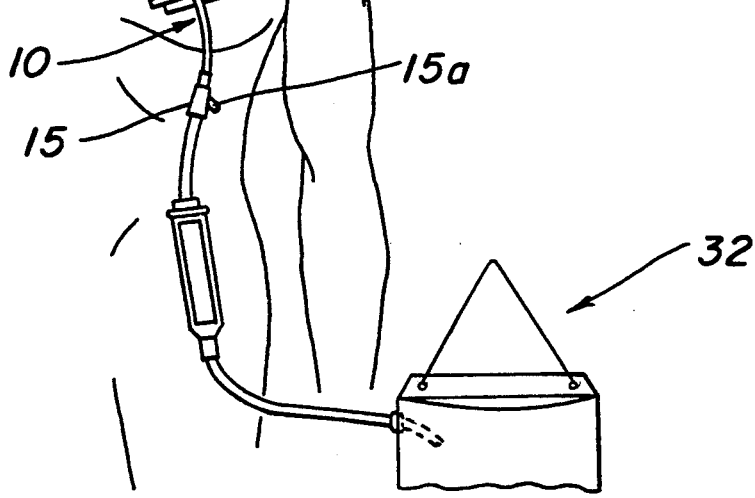
FIG. 6

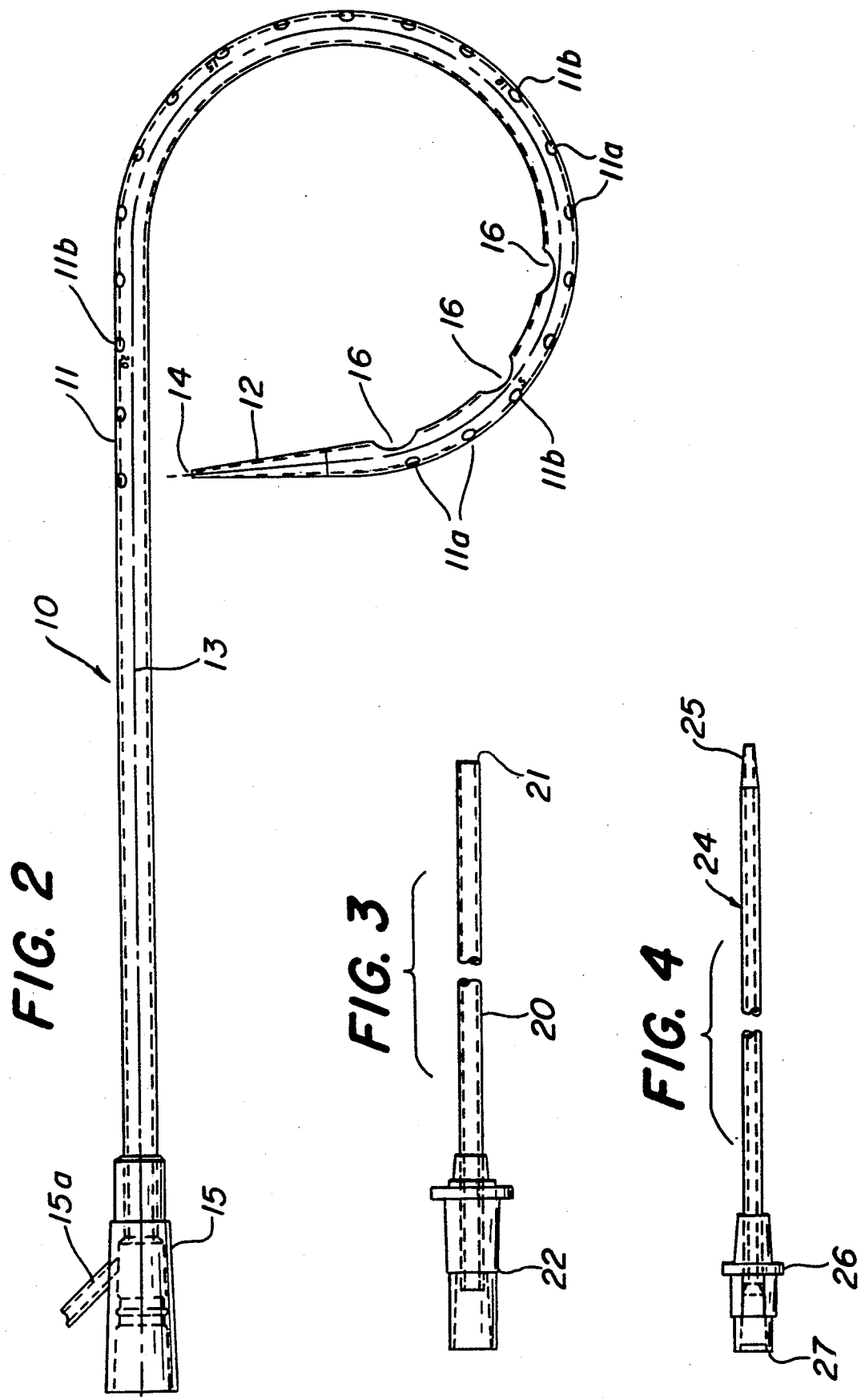

CATHETER ASSEMBLY

FIELD OF THE INVENTION

This invention relates to catheters, and although not limited thereto, particularly for catheters used for insertion into body cavities in living beings and, more particularly, to a catheter assembly which facilitates the percutaneous insertion of a catheter into a cavity in a safe, efficient and comparatively non-traumatic manner. The invention has particular applicability to the percutaneous insertion over a wire guide of relatively large diameter catheters made from soft pliable materials into human patients.

BACKGROUND OF THE INVENTION

Catheters for the drainage of body cavities, such as the bladder or the peritoneal cavity or the thoracic cavity, are known to the art. One example of such a catheter is provided as a set with a stiffening cannula which is inserted into an axial lumen extending to the distal tip region and has, as an additional second element, an elongated trocar stylet which is inserted through the stiffening cannula with its sharpened tip projecting through the distal tip of the catheter. The sharpened stylet tip is pushed through the skin and the cavity wall. Thereafter, the stylet is removed and a wire guide may be inserted through the stiffening cannula and the catheter advanced off of the cannula until it is properly placed within the cavity. The stiffening cannula and the wire guide are then removed, and the catheter is connected to the appropriate drainage system. Although the product described above is satisfactory for many applications, the size of catheter employed is relatively small in diameter since, in larger sizes, the pressure which must be applied to the proximal end of the catheter in inserting it into the cavity tends to cause the catheter material to bunch up on the stiffening cannula with the result that insertion becomes quite difficult and traumatic, particularly when catheters made of a very soft and pliable material are employed.

The prior art also includes U.S. Pat. No. 4,636,199 which discloses apparatus for inserting a catheter into the intercostal space of a human body for the removal of unwanted fluid, such as air or blood. According to the '199 Patent, a syringe having a hollow needle is first inserted into the intercostal space. After verification that the distal tip of the needle is within the space, the syringe is detached from the needle and a wire guide inserted through the needle lumen. The needle is then withdrawn over the wire guide and a catheter having an elongated trocar projected from its distal tip is threaded over the wire guide. The trocar has a flared proximal end portion which interfaces with a similar flared portion of the catheter. As the trocar is pushed into the cavity, the force is transmitted to the catheter and the two are moved as a unit into the intercostal space. The wire guide and the trocar are then removed, and the catheter is attached to the conventional suction or drainage equipment. Like the drainage set first described, the catheter material has a tendency to bunch up as the catheter is inserted, making insertion more difficult and more traumatic to the patient.

U.S. Pat. No. 2,828,744 to Hirsch et al discloses a vascular catheter in which a shoulder on a needle cooperates with a mating surface formed by the end of a sleeve so that the needle fits within what is termed an "external needle". The internal needle imparts stiffness to the end portion of the external needle to facilitate insertion into a blood vessel.

SUMMARY AND OBJECTS OF THE INVENTION

In accordance with the invention, a relatively long catheter of flexible material is inserted into a body cavity of a patient through use of a stiffening assembly which remains totally inside the catheter during the insertion procedure, thereby easing placement while minimizing the risk of tissue damage. Further according to the invention, the catheter is equipped with an internal abutment surface within the lumen of the catheter immediately adjacent to the distal tip. The stiffening assembly preferably includes a tapered portion which projects internally of the tip distally of the abutment surface so that even though the tip is made of a soft pliant material, it is stiffened during insertion. The stiffening assembly also includes a member having an end abutment portion which cooperates with the abutment surface within the catheter. The stiffening assembly extends lengthwise of the catheter and projects from its proximal end. By pressing on the proximal end of the stiffening assembly, insertion pressure is transmitted directly to the distal end of the catheter. This prevents bunching up of the catheter material as it is pressed into the cavity, providing a simpler and faster insertion technique which is less traumatic for the patient. Preferably, the assembly also includes a guide wire to facilitate insertion. Once the catheter is within the cavity, the stiffening assembly is removed and the catheter connected to a drainage or suction device.

Accordingly, an object of the invention is the provision of means including a removable stiffener assembly which facilitates the placement of a relatively large diameter catheter for the removal of fluids from a body cavity of a patient.

Another object of the invention is the provision of an assembly for the placement of a catheter within a body cavity utilizing a conventional Seldinger wire guide technique.

Still another object of the invention is the provision of means for insertion of large diameter pliable catheters which simplifies placement and reduces patient trauma.

Another object of the invention is a reduction of the risk of puncture of the wall of a body cavity during placement of a catheter.

A further object is to permit an increase in drainage capability through the use of larger diameter drainage catheters.

A still further object of the invention is the provision of a simpler, safer and faster method of placement of drainage catheters.

Other objects and advantages of the invention will become apparent from the following detailed description of an illustrative embodiment of the invention when read in view of the accompanying drawings.

SUMMARY OF THE DRAWINGS

FIG. 1 is a schematic view illustrating a drainage catheter incorporating the invention in preferred form as it is about to be inserted into the thoracic cavity of a patient;

FIG. 2 is a detail view of a drainage catheter formed in accordance with the invention;

FIGS. 3 and 4 are detailed views of a drainage catheter stiffening assembly formed in accordance with the invention;

FIG. 5 is a detailed view illustrating the distal tip of the catheter with the stiffening assembly fitted within the catheter lumen; and FIG. 6 is a view showing the catheter as inserted within the thoracic cavity and ready for use in the drainage of fluids from that cavity.

DETAILED DESCRIPTION OF THE ILLUSTRATIVE BODY OF THE INVENTION

With particular reference to FIGS. 1 through 5 and turning first to FIG. 2, a catheter 10 is illustrated comprising a body portion 11 of circular cross-section of substantially uniform diameter. The catheter further is provided with a tapered distal tip 12 and has a lumen 13 extending lengthwise thereof, the lumen exiting through a port 14 at the end of tapered distal tip 12.

A hub 15 is affixed to the proximal end of the catheter for connection of the catheter to suitable drainage equipment, such as a drainage bag or a suction device as is explained below. Preferably, a plurality of longitudinally spaced ports or openings 16 are formed in the catheter body at axially spaced locations proximally of the tapered distal tip. Each opening directly communicates with the lumen 13.

The catheter may also be provided with a branch line 15a provided, for example, for the purpose of infusion or sampling without disconnection of the drainage system. Line 15a is fitted with a luer fitting 15b and a clamp 15c which is used to close off line 15a when its use is not required.

Preferably, the catheter body is formed of polyurethane or other inert, relatively flexible material. Polyurethane has been found to be particularly useful for the purpose since it is biocompatible which assures excellent indwelling performance for extended use. In the preferred form of invention, the distal tip 12 is formed of a relatively softer and more pliant polyurethane material. The tip material is preformed and bonded to the body by heat fusion in accordance with techniques understood by those of ordinary skill in the art.

The distal region of the catheter body between the distal tip 12 and a point spaced proximally of the openings 16 is heat set so that it curves around upon itself when not restrained, as is illustrated in FIG. 2. The preformed curvature allows the catheter to curve according to the cavity shape. In a catheter with a preformed curvature, the lumen ports should be spaced along the inner surface of the curved catheter wall to assure that they are not blocked by the cavity wall.

Preferably, the body of the catheter is provided with axially spaced markings 11a and numerical indicia 11b, typically spaced at 1 and 5 cm intervals respectively so as to indicate to the physician placing the catheter the location of the distal tip within the patient. As is known in the art, the catheter body may be radio opaque so as to be easily detectible by x-ray.

Referring now to FIG. 5, lumen 13 is provided with an internal shoulder or proximally facing abutment surface 18 at the distal end of the body portion where the body portion joins the tip.

With reference to FIGS. 3 and 4, a catheter stiffening and insertion assembly is illustrated which preferably comprises a hollow elongated cannula 20 having a distal end surface 21 and a separate dilator member 24. Cannula 20 is sized so that it fits within catheter lumen 13.

When fully inserted within the lumen 13, as is illustrated in FIG. 5, it can be seen that the distal end surface 21 abuts against the proximally facing abutment surface 18 when the cannula is fully inserted. When in this position, the catheter is maintained in a straightened condition as is seen in FIG. 1.

A hub 22, which is preferably formed of a clear plastic material, such as acrylic, is affixed to the proximal end of cannula 20.

As noted above, the straightening and insertion assembly preferably further comprises a tip stiffening hollow dilator member 24, as is illustrated in FIG. 4. Dilator member 24 is dimensioned to slidably fit within the lumen of the cannula 20 and has a tapered distal tip 25 and a proximal hub 26 with a standard luer connector 27 at its proximal end. When the dilator member is fully inserted within the cannula 20, the tapered distal tip preferably substantially fills and conforms to the shape of the, inner surface of the catheter tip 12 and, thus, reinforces and stiffens the tip during the insertion procedure. However, the tip of the dilator member should terminate a sufficient distance proximally of the catheter tip so that the dilator tip cannot contact and possibly damage delicate tissue during catheter placement.

In use, the cavity to be drained is located and the intended puncture site prepared and draped in accordance with standard technique. Preferably, a hollow introducer needle is affixed to the end of a syringe of known type. The needle is inserted and the syringe assembly is aspirated to assure proper placement of the needle within the cavity. A wire guide is then advanced through the hollow needle to the required depth. Once the wire is properly located, the syringe is detached from the needle and the catheter drainage assembly with the stiffening assembly fully inserted, is threaded over the wire guide as shown in FIG. 1 wherein the wire guide is illustrated by the reference character 30. If desired, a dilator, not shown but preferably having graduations imprinted on its side wall, may be advanced into the cavity over the guide wire to the same depth as the introducer needle prior to threading of the catheter assembly. Upon removal of the dilator, the catheter assembly including the cannula 20 and dilator member 24 is then advanced over wire guide 30 by exerting axial pressure on the h b 22 and 26. By this means, the pressure applied is transmitted directly to the internal shelf within the lumen of the catheter until the catheter assembly is advanced to the same depth as the introducer needle and dilator, as is shown by the graduations on the catheter side wall. Once the catheter is inserted to the depth desired, the straightening assembly and the catheter are separated by maintaining the straightening assembly position and advancing the catheter. The wire and the straightening assembly are then removed as a unit. Proper catheter placement is assured by aspirating through the catheter when proper placement is determined the catheter is then connected to the appropriate drainage equipment 32, as is illustrated in FIG. 6.

By advancing the catheter through use of a stiffening assembly having an end abutment surface which interfaces with shelf or shoulder 18 with the tapered distal tip of the dilator reinforcing and straightening the soft pliant catheter tip, the catheter tip can be passed through the body tissue with minimal trauma to the patient. Because of the interfacing abutment surfaces, compressive stresses are not set up in the body of the catheter, thereby eliminating the tendency of the soft flexible material to bunch up. By use of this invention, the size of the catheter throughbore or lumen may be maximized, thereby increasing the flow capacity of the catheter. Because very soft tip materials may be utilized, tissue damage within the cavity is substantially reduced. This is of particular importance in the introduction of the catheter into the thoracic cavity since the risk of lung puncture is minimized.

What is claimed is:

1. A drainage catheter assembly for the insertion of a drainage catheter percutaneously, said assembly including a wire guide over which the catheter is adapted to be guided into a body cavity, said assembly comprising:
   an elongated catheter having a tapered distal tip, the tip being comprises of soft, pliant polymeric material, a central lumen extending length wise of the catheter and exiting at the distal tip, said catheter having a side port spaced adjacent to the tip, said side port being in communication with the lumen;
   said catheter having a proximally facing annular abutment shoulder within said lumen, said abutment shoulder being spaced between the distal end of the distal tip and said side port;
   a stiffening cannula slidably received within the lumen, said stiffening cannula having a distal tip of the stiffening cannula abutting said shoulder when the stiffening cannula is fully inserted within the lumen; and
   a removable dilator extending lengthwise of the catheter, said dilator being adapted to slidably fit within the stiffening cannula, said dilator having a throughbore, the assembly comprising the catheter, the stiffening cannula and the dilator being threaded over the wire guide for percutaneous placement within the body cavity.

2. The assembly according to claim 1 wherein said dilator has a rigid tip terminating beyond the distal end of the stiffening cannula within the catheter tip for stiffening the pliant catheter tip during percutaneous insertion of the catheter.

3. The assembly according to claim 2 further including a plurality of axially spaced side ports in communication with the lumen.

4. The assembly of claim 3 wherein said distal end of said dilator tip terminates within the distal catheter tip.

5. The assembly of claim 4 wherein said catheter has a preset curvature within a zone extending lengthwise of and extending to a point from the distal tip to a point just proximal of said side ports, said zone assuming said curvature upon removable of said stiffening cannula and said dilator.

6. In combination:
   an elongated drainage catheter having a tapered distal tip comprising a soft pliant material and a flexible body portion of uniform outer diameter which is stiff relatively to said tip;
   a central lumen extending lengthwise of the body portion of the catheter and exiting at the distal tip;
   a plurality of side ports adjacent the tip, said side ports being in communication with the lumen and being axially spaced from one another;
   a proximally facing abutment surface within said lumen;
   a removable hollow stiffening assembly adapted to slidably fit within said catheter lumen and extending lengthwise thereof, said stiffening assembly having a tapered distal tip portion adapted to stiffen said tapered distal tip of said catheter and a distally facing surface portion proximally of said tapered distal tip portion and being adapted to interface with said proximally facing abutment surface, said stiffening assembly being relatively dimensioned to transmit pressure applied to the proximal end of the stiffening assembly directly to said abutment surface, the tapered distal tip portion of said stiffening assembly terminating within the tapered distal tip of the catheter.

7. The combination according to claim 6 wherein said stiffening assembly comprises a hollow stiffening cannula and a dilator slidably received within said hollow stiffening cannula, said tapered distal tip portion being integral with said dilator and said surface portion being a flattened end portion of said stiffening cannula.

8. The combination according to claim 7, wherein said dilator includes a wire guide lumen extending lengthwise therethrough and a wire guide adapted to extend through the wire guide lumen, through the catheter tip into a drainage cavity.

9. The combination of claim 8 wherein said catheter has a preset curvature within a zone extending lengthwise of and extending from the distal tip of said catheter to a point just proximal of said side ports, said zone assuming said curve upon removable of said stiffening cannula and said dilator.

10. The combination of claim 9 further including axially spaced markings extending lengthwise of the catheter from the tip of the catheter for indicating the extent of insertion of the catheter into the cavity.

11. The combination of claim 10 wherein the said side ports are positioned on the inside surface of the curvature of said zone.

12. The combination according to claim 7 wherein said catheter has a proximal hub and a branch line connected to said hub and being in communication with said lumen for withdrawing samples and for administration of medicaments.

* * * * *

UNITED STATES PATENT AND TRADEMARK OFFICE
CERTIFICATE OF CORRECTION

PATENT NO. : 5,205,830

DATED : April 27, 1993

INVENTOR(S) : Dassa et al

It is certified that error appears in the above-identified patent and that said Letters Patent is hereby corrected as shown below:

Column 4, lines 33 and 34, delete "is detached from" and insert --and--; after "needle" insert --are removed--

Column 4, line 45, "h b" should be --hubs--

Column 4, line 56, after "catheter" insert --.--; change "when" to --When--

Column 5, line 14, "comprises" should be --comprised--

Column 5, line 15, change "length wise" to --lengthwise--

Column 5, line 49, "removable" should be --removal--

Column 6, line 39, "removable" should be --removal--

Signed and Sealed this

Fourth Day of January, 1994

Attest:

BRUCE LEHMAN

Attesting Officer     Commissioner of Patents and Trademarks